(12) United States Patent
Moses (10) Patent No.: US 9,460,596 B1
(45) Date of Patent: Oct. 4, 2016

(54) PORTABLE WIRELESS REMOTE MONITORING AND CONTROL SYSTEMS

(71) Applicant: Thomas Lawrence Moses, Greenville, SC (US)

(72) Inventor: Thomas Lawrence Moses, Greenville, SC (US)

(*) Notice: Subject to any disclaimer, the term of this patent is extended or adjusted under 35 U.S.C. 154(b) by 0 days.

(21) Appl. No.: 15/075,061

(22) Filed: Mar. 18, 2016

(51) Int. Cl.
*H04N 7/15* (2006.01)
*G08B 13/196* (2006.01)
*H04N 7/14* (2006.01)

(52) U.S. Cl.
CPC ..... *G08B 13/19695* (2013.01); *G08B 13/1966* (2013.01); *H04N 7/14* (2013.01)

(58) Field of Classification Search
USPC ...................................... 348/14.05, 154, 155
See application file for complete search history.

(56) References Cited

U.S. PATENT DOCUMENTS

| | | | |
|---|---|---|---|
| 6,542,078 B2 | 4/2003 | Script et al. | |
| 6,828,909 B2 | 12/2004 | Script et al. | |
| 7,394,385 B2 | 7/2008 | Franco, Jr. et al. | |
| 7,964,989 B1 | 6/2011 | Puschnigg et al. | |
| 8,217,790 B2 | 7/2012 | Script | |
| 8,374,729 B2 | 2/2013 | Chapel et al. | |
| 8,421,624 B2 | 4/2013 | Hsu | |
| 2010/0217096 A1 | 8/2010 | Nanikashvili | |
| 2011/0317007 A1* | 12/2011 | Kim | G08B 17/10 348/143 |
| 2016/0232942 A1* | 8/2016 | Godtland | G11B 27/28 |

FOREIGN PATENT DOCUMENTS

| | | |
|---|---|---|
| CN | 102736587 A | 10/2012 |
| CN | 202939450 | 5/2013 |
| WO | WO2013/155559 | 10/2013 |

* cited by examiner

*Primary Examiner* — Creighton Smith
(74) *Attorney, Agent, or Firm* — Southeast IP Group, LLC.; Thomas L. Moses (57) ABSTRACT

A user-programmable portable wireless remote monitoring system includes a base unit a series of sensor units and a remote control device. The base unit is connected to the internet, and receives wireless alerts from sensor arrays deployed in the sensor units. When the sensor units detect a problem, then they send an alert to the base unit, which then relays the alert to the remote control device that is preferably a smart phone, tablet, or the like, including software for operating the system. The system may also incorporate smart outlets that are remotely operable by the remote control device, various monitors, a touchscreen, and wearable tracking devices to monitor a person within the home. The system is designed to provide security, home system monitoring, personal medical monitoring, and remote control of various electrical appliances, as well as providing alerts of problem situations sent to the remote control device.

16 Claims, 3 Drawing Sheets

PORTABLE WIRELESS REMOTE MONITORING AND CONTROL SYSTEMS

BACKGROUND OF THE INVENTION

Home security and monitoring systems have become enormously popular, and in many ways necessary, across the United States and the world in recent years. Different types of systems are used for different purposes. For instance, security systems are generally used to make sure that if the user's home, office, or other structure is broken into, the system may alert the user and/or a monitoring service, so that action can be taken to stop the crime in progress. Additionally, security systems may include lights and sirens to alert neighbors and to deter criminals from spending any more time in the vicinity of the screaming alarms and flashing lights.

In recent years, another type of home monitoring system has become available, wherein the system is used to monitor people and their health. These types of systems generally include a wearable device that is worn by the person whose health is to be monitored, and the wearable device includes sensors that may keep track of and record the user's heart rate, blood pressure, calories burned, along with many other factors. The wearable device may also be used to transmit data wirelessly to a receiving station, particularly if any of the factors fall outside of normal parameters. For instance, if a wearable device senses that a person's blood pressure is dangerously high, the wearable device may transmit a message to the receiving station, which may then relay the message along to medical personnel, a caregiver, a relative or a friend.

Another type of home monitoring system is used to monitor remote properties that may be vacant for extended periods of time, such as vacation homes, rental apartments or condominiums, or the like. Although these systems often do include a security component, they also may include monitors to make sure that major components of the home are working properly. These systems may include temperature monitors to ensure that the temperature inside the home does not fall below freezing during the winter, which may result in frozen or burst pipes within the plumbing. Additionally, other types of sensors may be employed to ensure normal operation, including sensors for monitoring water usage, electricity usage, humidity, smoke detectors, carbon monoxide detectors, and the like.

Various types of security and monitoring systems are also beginning to include "smart house" features, which allow a user to remotely control lighting, appliances, entertainment systems, environmental systems, and the like via smart phones, tablets, or computers.

The following is a list of patents or patent related documents that relate generally to monitoring systems, remote control of electrical devices, and security systems. Each of the following references is hereby incorporated herein by reference:

U.S. Pat. No. 8,421,624—Home Security System

A home security system includes a plurality of monitoring assemblies each comprising a data communication device, a light, a video camera, a transmitter, a sensor, a loudspeaker, a warning device, an identification device, a projector, an adjustment device for adjusting angles of the light, the video camera, and the projector, and a power supply; a fixed controller comprising a data communicating device and a data storage device; and a hand-held portable controller comprising a wireless communication module and an equipment set module. The fixed controller is adapted to activate the monitoring assemblies. The hand-held, portable controller is adapted to remotely activate the monitoring assemblies.

Application No. CN 102736587 A—Monitoring and Control Alarming System for Smart Home The invention discloses a monitoring and control alarming system for a smart home. The system comprises a control host arranged in an indoor environment, environmental temperature, humidity and toxic gas monitoring equipment, a wireless switch and a portable software terminal. Human health monitoring equipment and a personnel positioning tag are also arranged in the system, wherein the human health monitoring equipment is used for monitoring human health conditions comprising blood pressure, a heart rate and body temperature in real time, and providing a data monitoring interface. A home monitoring and control function is realized, and in addition, problems about the health monitoring and real-time positioning of family members are solved.

U.S. Pat. No. 6,828,909—Portable Motion Detector and Alarm System and Method

A portable security alarm system which can be installed on a temporary basis and removed from an object whose movement is to be detected including a motion detecting and radio signal transmitting member for mounting proximate the object whose movement is to be detected, a member for selectively coupling and decoupling the motion detecting and radio signal transmitting member relative to the object whose movement is to be detected, a combined radio signal receiving and alarm generating member for receiving a signal from the combined motion detecting and radio signal transmitting member and producing an alarm, a remote control for actuating and deactivating the radio signal receiving and alarm generating member, and components for providing object identification information identifying the object whose movement is to be detected and distance measurement information for measuring the distance moved by the object.

U.S. Pat. No. 6,542,078—Portable Motion Detector and Alarm System and Method

A portable security alarm system which can be installed on a temporary basis and removed from an object whose movement is to be detected including a motion detecting and radio signal transmitting member for mounting proximate the object whose movement is to be detected, a member for selectively coupling and decoupling the motion detecting and radio signal transmitting member relative to the object whose movement is to be detected, a combined radio signal receiving and alarm generating member for receiving a signal from the combined motion detecting and radio signal transmitting member and producing an alarm, a remote control for actuating and deactuating the radio signal receiving and alarm generating member, an information gathering device adapted to receive the predetermined signal, to gather information relating to the movement, and to transmit the information, and a remote notification device adapted to receive the information from the information gathering device, to establish data communication with a remote host and to provide the information to the remote host.

U.S. Pat. No. 8,217,790—Portable Motion Detector and Alarm System and Method

A portable security alarm system including a movement detecting and signal transmitting member for mounting on or proximate to the object whose movement is to be detected, a signal receiving and alarm generating member for receiving a signal from the movement detecting and signal transmitting member and producing a security response, a remote control for actuating and deactivating the signal receiving and alarm generating member, art environmental monitoring member for sensing an environmental condition and providing a signal to the signal receiving and alarm generating member, a visual information gathering member for gathering visual information and providing a signal to the signal receiving and alarm generating member, an audio output member for receiving a signal from the signal receiving and alarm generating member and generating an audio output, and components tor delivering a security notification to remote recipients. A security network that includes the alarm system is also disclosed. An inertial sensor for alarm system or for activating or deactivating a device is additionally disclosed.

Patent No. CN 202939450—Household Electricity Quantity Monitoring System

The utility model relates to a household electricity quantity monitoring system. The household electricity quantity monitoring system comprises an intelligent terminal, a gateway, electricity quantity metering sockets which are used for measuring electricity quantity data, and a household appliance adapter which is used for switching and controlling household appliance modes. The household electricity quantity monitoring system is characterized in that sockets of household appliances are plugged into the electricity quantity metering sockets; the household appliance adapter is connected to the household appliances; the electricity quantity metering sockets and the household appliance adapter are in communications with the gate way through a wireless network One; the gateway is in communication with the intelligent terminal through a wireless network Two; and bidirectional communications are established between the electricity quantity metering sockets and the household appliance adapter with the intelligent terminal through the gateway. The household electricity quantity monitoring system has the following characteristics that: 1) the ZIGBEE network is adopted so as to summary used electricity quantity data of the scattered metering socket and the household appliances, and thus power acquisition and work modes of the household appliances are controlled, long standby time is shortened and service life is prolonged; 2) through the intelligent terminal (with a WIFI module), overall electricity quantity monitoring and management control of the household appliances are realized; and 3) the ZIGBEE is adopted for adaptation to the WIFI protocol, and complexity of the gateway is simplified and mobile adaptability of the entire control system is expanded, U.S. Pat. No. 7,964,989—Method and System for Controlling Power to an Electrically Powered Device A system and method for remotely controlling power to an electrically powered device in a simple and efficient manner is disclosed herein. The system comprises an apparatus, an electrically-powered device and a controller. The apparatus comprises a cord, an alternating current outlet socket, an alternating current input plug, a latching relay, a processor and a transceiver. The system preferably uses a WiFi communication signal to transmit commands from the remote controller to the apparatus.

WO PCT No. WO2013155559 A1—A Programmable Electrical Control Device

A programmable electrical control device (10) adapted to be programmed by an external programming device, the programmable electrical control device for controlling electrical power supply in cooperation with an electrical switching device (12), the electrical switching device having a body, an electrical power supply input, an electrical power supply output (15) and a manual switch (16), the device (10) including a data connection module; memory; a timing module; a processor; and a switching module, including at least one supply on period, and at least one supply off period, wherein at least a part of the device (10) is capable of being integrated within the body.

U.S. Pat. No. 8,374,729—Smart Electrical Outlets and Associated Networks

A control system (300) allows recognized standard premise electrical outlets, tor example NEMA, CEE and BS, among others to be remotely monitored and/or controlled, for example, to intelligently execute blackouts or brownouts or to otherwise remotely control electrical devices. The system (300) includes a number of smart receptacles (302) that communicate with a local controller (304), e.g., via power lines using the TCP/IP protocol. The local controller (304), in turn, communicates with a remote controller (308) via the internet.

U.S. Pat. No. 7,394,385—Comprehensive Monitoring System

A monitoring system for physically challenged clients can have a base hub unit, one or more sensor units, one or more repeater units, and a mobile unit for a client to wear in a residential setting. In an institutional setting, a mobile repeater can be used for monitoring outside premises. A three-axis accelerometer can be used to detect falls and to monitor for other life activities, such as sleeping.

Publication No. 20100217096 A1—A Health Monitor and A Method for Health Monitoring A method for health monitoring and a personal health monitor that includes: a band that comprises at least one biometric sensor; and a data connector adapted to fasten a first end of the band to a second end of the band, and is also adapted to be connected to a reception device such as to provide data to the reception device; wherein the data connector is coupled to the at least one biometric sensor.

Most of the residential and commercial monitoring systems available today are expensive and difficult to install, requiring in-wall wiring and trained technicians to perform the installation work. Additionally, once installed, it is difficult to uninstall the systems and move them to another location. Further, many of these existing systems require users to pay a monthly subscription for the monitoring services, which is more expensive than many people can afford. None of the prior art incorporates a system that can provide security features, personnel monitoring, home systems monitoring and remote control smart house capabilities.

Therefore, it would be advantageous to provide a programmable wireless remote monitoring and control system that is easy to install and set up, requiring no wiring, and which is portable, so that a user can easily unplug and remove the components from one location and quickly set the system up in another location. Moreover, it would be desirable to provide a system that monitors against burglary and trespass, as well as monitoring people with high-risk medical conditions, and further, that monitors the electrical, plumbing and environmental systems to ensure proper operation. Finally, it would be desirable to provide such a system described above, which would also allow a user to remotely control (either from within the home or building, or from many miles away) certain appliances, lighting, and other electrical devices, and to have the ability to incorporate these electrical devices into the monitoring system, in any desired manner. Finally, it would be desirable to provide a system that may be easily programmed by a user to perform various functions, such as macro functions for controlling multiple appliances with one command (or the press of a single button or icon on the remote control), or to perform functions in response to alerts generated by the system.

BRIEF SUMMARY OF THE INVENTION

In accordance with one aspect of the invention, a first embodiment of a home monitoring system includes a base unit and a series of sensor units that collect information and wirelessly transmit the collected information back to the base unit. The base unit may also include sensors of its own. In the first embodiment, the base unit simply plugs into a standard electrical outlet, and includes a plurality of remotely controllable smart electrical outlets that may be used to power appliances, lights, or the like. The base unit also preferably includes means for two-way communication with the sensor units, as well as a transceiver for sending and receiving information over a wireless internet network. The base unit may also include its own sensor array for monitoring and collecting information and data.

The base unit may be connected via wireless communication through the internet with a computer and/or a hand held device, such as a smart phone, tablet, or the like, which serves as a remote control. The remote control may receive information from the base unit, and may also act as a control for the base unit and sensor units. Preferably, the remote control includes software (an "app") that serves as the interface between the user and the remote monitoring and control system.

The sensor units, in a preferred embodiment, also include a series of standard electrical remotely controllable smart outlets, as well as means for two-way communication with the base unit. Instructions from the remote control may be received by the base unit, and then relayed to the sensor units. The sensor units may include multiple types of sensors, including motion sensors, a camera still shot and/or video), heat sensors, humidity sensors, standing water sensors, laser sensors, smoke detectors, carbon monoxide detectors, microphones, or any other suitable sensors.

The sensor units provide constant monitoring, and are in either constant or periodic communication with the base unit. The base unit may be programmed to ignore data that falls within acceptable parameters such as temperature in the range of 40° to 90° Fahrenheit, for instance), but to send an alert to the user if the data falls outside the acceptable parameters (temperature dips below 40° F., for instance).

In one embodiment, if the motion sensor senses motion, then the sensor unit may be programmed to 1) activate the camera to take a photo, a series of photos, or a short video, and 2) transmit the visual data to the base unit, which then relays the visual data to the user via the remote control in the form of an alert. It is further contemplated that a microphone may be included in the sensor unit, so that the short video transmission may also include sound, as well.

An additional feature of the system is that the remote control may also be used to control the smart electrical outlets of the base unit and the sensor units. For instance, if a lamp is plugged into a smart outlet on the base unit (or on a sensor unit), the user may be able to cut the lamp on or off remotely using the remote control with the software app on a smart phone, tablet, or other remote control device. It is also contemplated that the sensor unit may be programmed to activate one or more smart outlets in response to data picked up by the sensors. For example, if a motion sensor in a sensor unit detects motion, then the sensor unit may be programmed to activate one or more of the smart outlets (either plugged into that specific sensor unit, another sensor unit, or the base unit) to switch on one or more lamps or lights immediately upon sensing the motion.

Other wirelessly operated components may be incorporated into the system, such as door and window sensors to determine when a door or window has been opened, and to monitor the status of whether doors and windows are in an open or closed position. A siren or audible alarm may also be incorporated into the system, so that it may be activated upon any of the motion sensors detecting motion within the protected area. Each of these components is preferably battery operated, and communicates wirelessly with the base unit. A wireless panic button may be incorporated into the system as well, so that if a user that is in the protected area is in distress, they may depress the panic button to activate the alarm and/or send an alert to a monitoring system, another user, the police, or any other chosen recipient.

In one embodiment, the base unit (or touchscreen) may include a microphone and speaker assembly, so that a person can communicate through the base unit or touchscreen unit with the remote control device using video and audio communications.

Another embodiment of the system includes the ability to monitor certain aspects of a person's health and well-being, preferably through the use of a wearable device that communicates wirelessly with the system. In recent years, wearable devices have become commonplace, and may be used to monitor a wearer's heart rate, blood pressure, number of stairs climbed or miles walked, and other measures of a person's daily activities and body functions. Such a wearable device may be incorporated into the system, so that the wearable device can wirelessly communicate with the sensor units and base unit in order to provide information and data about the wearer's health and activity. Certain parameters may be programmed into either the wearable device or the base unit, so that if any measured data falls outside normal parameters (heart rate is too high, or blood pressure is too high, for instance), then the system may be programmed to send an alert for help to any desired person or entity, such as a family member, first responders, caregivers, security monitoring company or the like. It is contemplated that such a system may be employed by a family to monitor an elderly family member who still lives alone, so that they may be alerted remotely if a medical emergency or situation arises. The base unit and sensor units may directly monitor the wearer's movements around the house, and further, may receive data transmitted wirelessly from the wearable device. When the data falls outside of normal parameters, then the system can generate an alert to be sent out to a desired party to come check on the wearer, and render aid, if necessary.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE INVENTION

Overview

The present invention includes, in a first embodiment, a base unit 22 that plugs into a standard electrical outlet, along with a series of sensor units 10. The base unit 22 and the sensor units 10 include means for two-way communications, so that the sensor units 10 may transmit data collected by the sensors to the base unit 22, and the base unit 22 may transmit data or instructions to the sensor units 10. Preferably, the transmissions are wireless, and may be any type of wireless communications, including Bluetooth, radio frequency, sonar, laser, or any other suitable type of wireless communication.

As used herein, the terms "wi-fi," "wifi" or "WIFI" mean generally a local area wireless computer networking technology that allows electronic devices to connect to the network, mainly using the 2.4 gigahertz (12 cm) UHF and 5 gigahertz (6 cm) SHF ISM radio bands.

The Wi-Fi Alliance defines Wi-Fi as any "wireless local area network" (WLAN) product based on the Institute of Electrical and Electronics Engineers' (IEEE) 802.11 standards. However, the term "Wi-Fi" is used in general English as a synonym for "WLAN" since most modern WLANs are based on these standards."

Many devices can use Wi-Fi, e.g. personal computers, video-game consoles, smartphones, digital cameras, tablet computers and digital audio players. These can connect to a network resource such as the Internet via a wireless network access point. Such an access point (or hotspot) has a range of about 20 meters (66 feet) indoors and a greater range outdoors. Hotspot coverage can be as small as a single room with walls that block radio waves, or as large as many square kilometres achieved by using multiple overlapping access points.

As used herein, the term "bluetooth" is generally defined to mean a wireless technology standard for exchanging data over short distances (using short-wavelength UHFradio waves in the ISM band from 2.4 to 2.485 GH) from fixed and mobile devices, and building personal area networks (PANs). It can connect several devices, overcoming problems of synchronization.

As used herein, the term "touchscreen" is generally defined to mean an input device normally layered on the top of an electronic visual display of an information processing system. A user can give input or control the information processing system through simple or multi-touch gestures by touching the screen with a special stylus/pen and-or one or more fingers. Some touchscreens use ordinary or specially coated gloves to work while others use a special stylus/pen only. The user can use the touchscreen to react to what is displayed and to control how it is displayed; for example, zooming to increase the text size.

Figure 4:
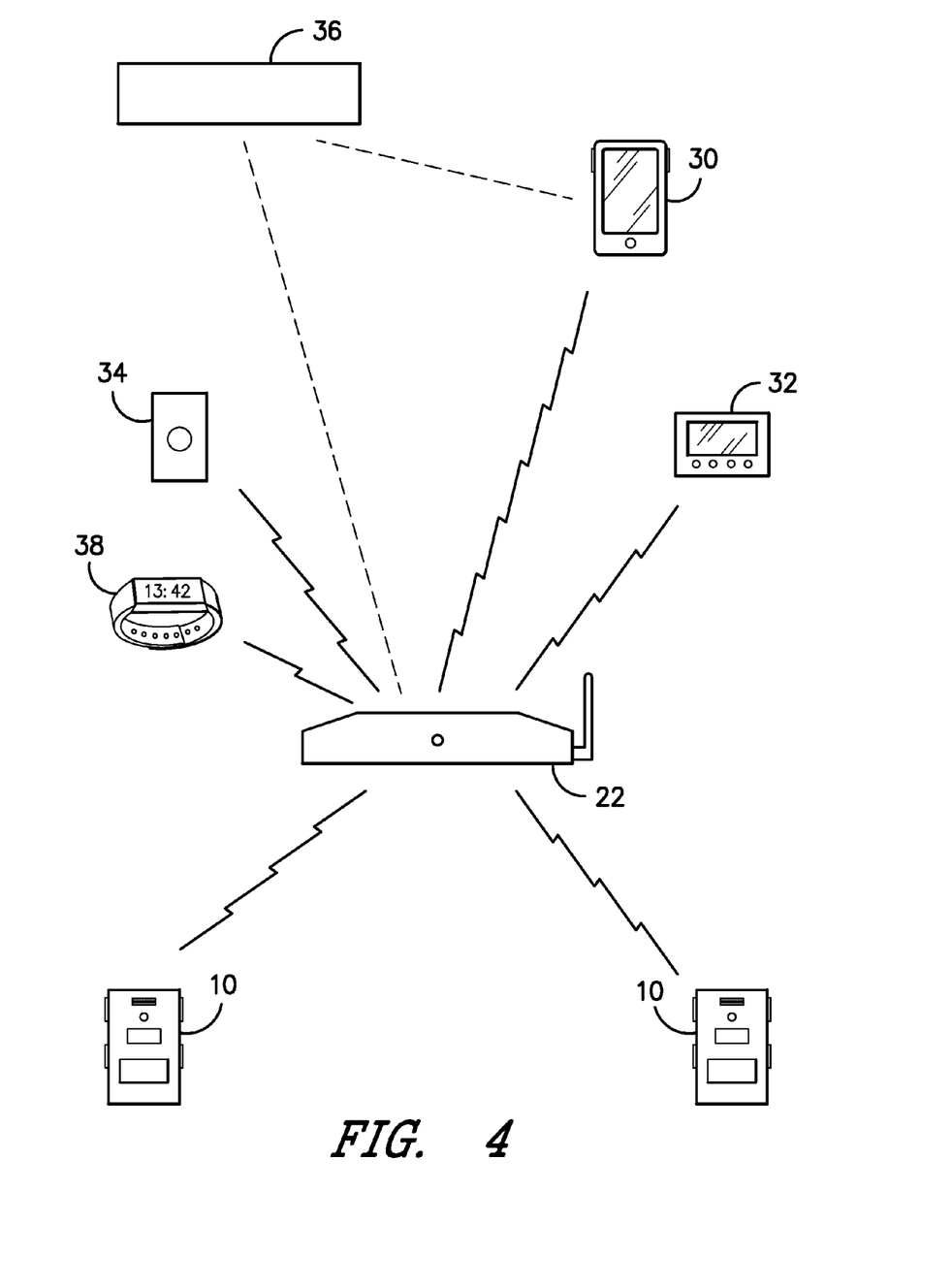
FIG. 4 is a schematic view of a base unit in wireless communication with a pair of sensor units, a touch pad for controlling the system, a remote control that may also be used to control the system, a panic button, and a remote server that receives and records data sent by the base unit.

The touchscreen 32 enables the user to interact directly with the display, rather than using a mouse, touchpad, or any other intermediate device (other than a stylus, which is optional for most modern touchscreens).

Touchscreens are common in devices such as game consoles, personal computers, tablet computers, electronic voting machines, and smartphones. They can also be attached to computers or, as terminals, to networks. They also play a prominent role in the design of digital appliances such as personal digital assistants (PDAs)es and some books (E-books).

Figure 2:
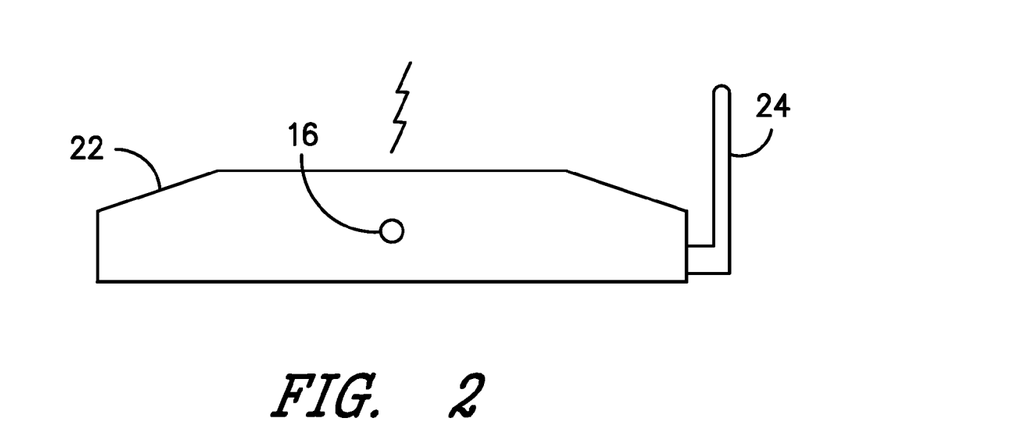
FIG. 2 is a front view illustration of one embodiment of a base unit, showing a camera and an antenna.

The base unit 22 preferably includes along with means for communicating with the sensor units 10, means for connecting to the internet, so that the base unit 22 can receive commands remotely from a remote control device 30, such as a smart phone, tablet, computer, or any other type of internet-connected remote control device. Additionally, the base unit 22 may include means of transmitting data and information through the internet, either to a monitoring service, a remote control device 30, a remote server 36, or the like. The base unit 22 may also include one or more sensors. The intern& connection may include a standard network connection, a wifi connection through a wireless router, or a cellular connection that allows internet communication through standard cellular networks, similar to the internet connection of most smart phones. In one preferred embodiment, the base unit 22 includes both a wifi internet connection and a backup cellular network data connection, similar to commonly found tablets and smart phones.

Figure 1:
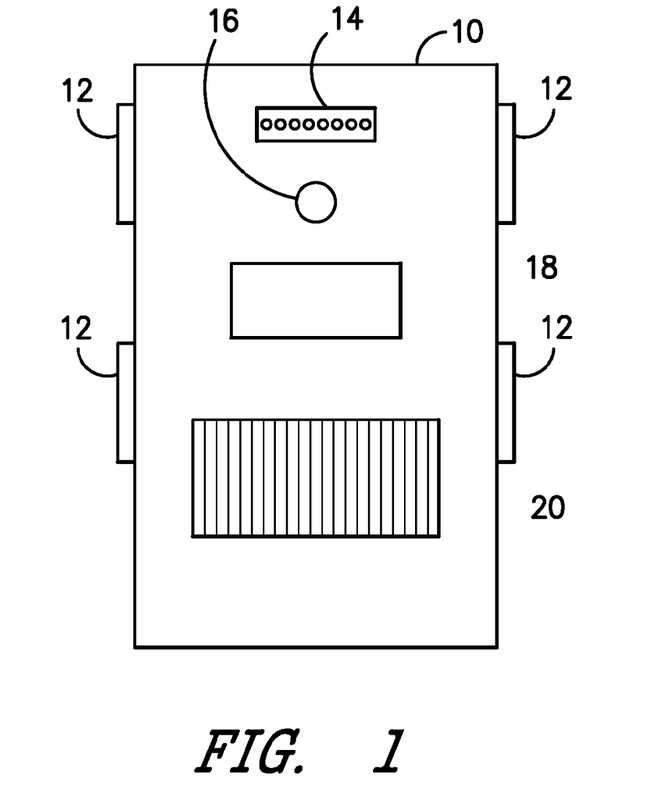
FIG. 1 is a front view illustration of one embodiment of a sensor unit having a series of LED lights, a camera, a motion detector, a speaker/audio alarm, and a series of smart outlets.

The sensor units 10 may include any of a variety of different sensors, as a part of an overall sensor array. Such sensors may include motion detectors 18, a camera 16, a microphone, temperature sensors, electrical usage sensors or meters, humidity sensors, electrical power sensors, standing water sensors, or any other suitable sensors or monitors. The sensor units 10 may also include a light 14 that may be used for a night light, or may be used as a camera flash. Preferably, the light 14 includes a series of LED lights, which may be controlled remotely. The lights 14, in a preferred embodiment, may be remotely switched on or off, dimmed or brightened remotely, or may be programmed lo light up upon alert or motion detection. The sensor units 10 and/or the base unit 22 may include an audio speaker 20, as well, to be used as an audio alarm if motion is detected. Additionally, the sensor units 10 and/or base unit 22 may include adjustable antennas 24.

The sensor units 10, in one embodiment include a standard electrical plug for plugging into a standard electrical outlet, and may include a series of standard electrical remotely controllable smart outlets 12 that may be used to power any electrical appliance, such as lamps, televisions, or the like. Preferably, the smart outlets 12 on the sensor units 10 may be operated remotely, by receiving commands or instructions from a remote control device 30 via the internet, so that if a user plugs a lamp into one of the smart outlets 12 on the sensor unit 10, for instance, the user may switch that lamp on or off (or potentially use a dimmer function) via the software app on their smart phone or tablet (remote control device 30).

Other wireless components may be incorporated into the system, as well. These components may he powered by plugging into a standard electrical outlet, or may be battery operated (or may include a battery backup in case of power failure). Such components include laser sensors, magnetic sensors, a keypad and screen (or touchscreen 32) for operating the system, a panic button 34, stand-alone motion sensors, smoke detectors, carbon monoxide detectors, and an audible alarm 20. In a preferred embodiment, each of these components also includes a battery monitor, and is configured to send an alert to the user via remote control 30 whenever a battery is running low, and preferably before the battery is dead, so that the user has an opportunity to change the battery before it completely runs out of power. Each of these wireless components may include a wireless transmitter that communicates with the base unit in order to provide an alert to any programmed condition, so that the base unit 22 can then relay the alert to the user remotely over the internet via the remote control 30.

In one embodiment, the sensor units 10 and the base unit 22 communicate with one another using Bluetooth technology, and the base unit 22 communicates with the remote control 30 over an internet connection, using either a wifi connection or a cellular data connection (similar to data connections used by smart phones in the absence of a wifi connection), or both. It is contemplated, however, that other types of communication may be used, both between the base unit 22 and the sensor units 10 (or other wireless components), as well as communications between the base unit 22 and a remote control device 30.

Security

Figure 3:
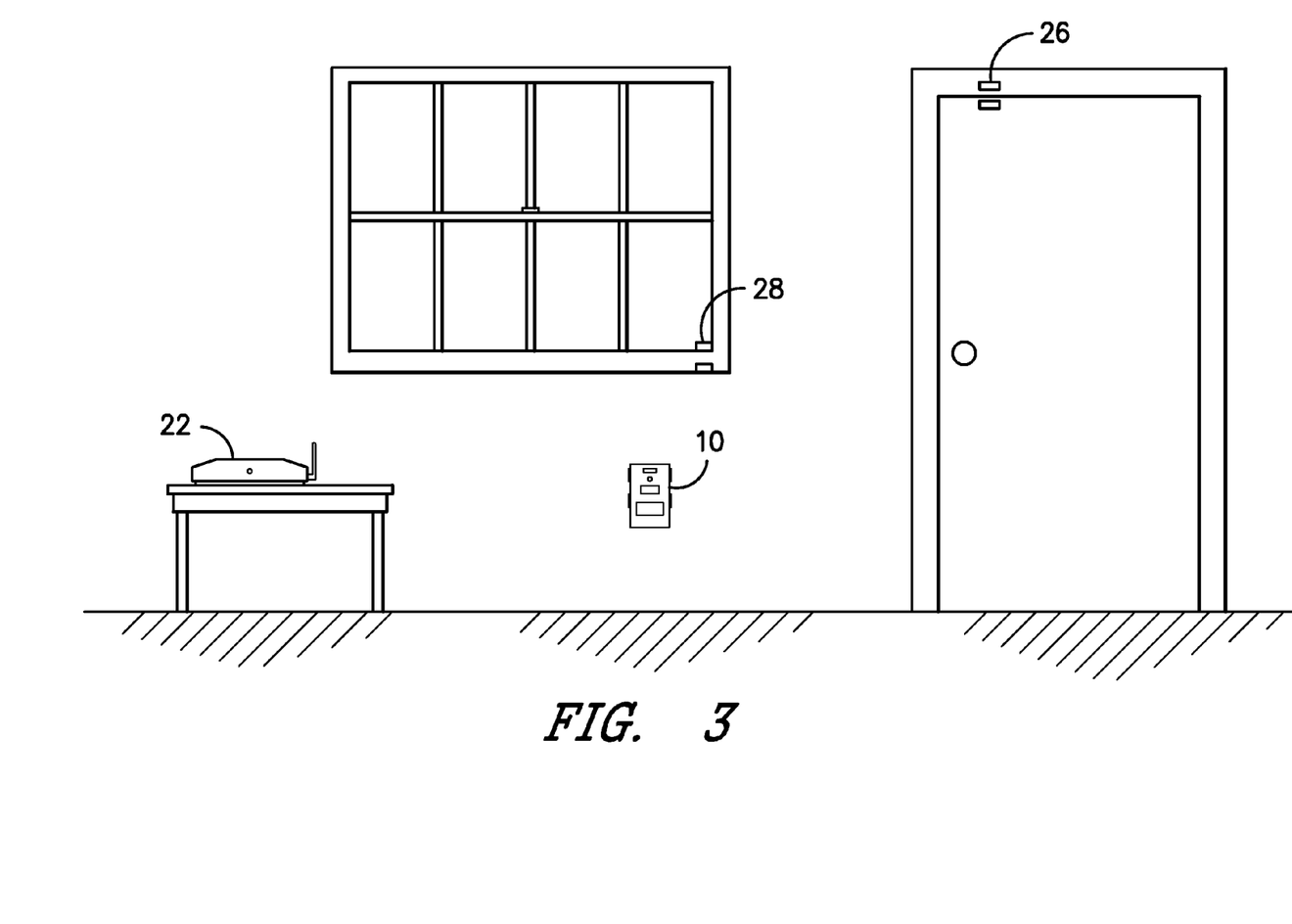
FIG. 3 is an illustration of a room having and a door, further showing a door sensor attached to the door and frame, a window sensor attached to a window and frame, a sensor unit plugged into a standard electrical outlet on a wall, and a base unit that wirelessly communicates with the sensors.

In use, the base unit 22 is simply plugged into an electrical outlet, and the sensor units 10 are plugged into other electrical outlets throughout the home, apartment, or buildin. In one embodiment, the user may download a software app onto her smart phone or tablet (remote control 30), and establish a connection (Bluetooth, for instance) between the phone and the base unit 22. Then, the user can establish a connection between a wireless (wifi) network and the base member 22, and enter a wifi password, if necessary. Once the wireless network connection is established with the base unit 22, the system becomes operational. It is also contemplated that the system may communicate with a cellular data network, either instead of, or as a backup to, a wifi network.

When a user leaves the building, she may use the software app to arm the system, which activates the sensor units 10 in the "Away" mode. In Away mode, the motion sensors 18 are activated to detect motion inside the home. The system may be programmed by the user so that any motion detected by the motion sensors 18 may trigger a number of responses. For example, if motion is detected, the motion sensor 18 may send an alert signal to the base unit 22, which then relays that message through the internet (or cellular) network to the user's software app on her phone or tablet (remote control 30). Additionally, detected motion may also activate the camera 16 to either 1) immediately take a still photo, 2) take a series of still photos, 3) take a short video, and/or 4) simply allow the user, upon receiving the alert, to view footage from the camera 16 in real time. In one embodiment, the sensor unit may include a microphone, so that sound may be transmitted and/or recorded along with video.

Additionally, the sensor units 10 may be programmed by the user to activate any or all of the smart outlets 12 of the sensor unit 10 (or other sensor units 10) to remotely switch on, which will switch the lights on in the room where motion was detected. The sensor unit 10 may include an audible alarm 20, as well, which may be triggered upon detecting motion. Alternatively, a separate audible alarm may be wirelessly incorporated into the system.

The system may also include a "Home" mode. In "Home" mode, the door sensors 26, window sensors 28, panic button 34, and other security features are active, while the motion sensors 18 are not. In this way, people can move about the building while the system is in the Home mode without setting off the alarm, but door sensors 26, window sensors 28, panic button 34 and other features of the system are still active.

Other security components may be incorporated into the system, as well. For example, a laser sensor may be employed in several different ways to detect intruders. The laser sensor may include a laser or infrared transmitter, and a laser or infrared detector. Essentially, the laser emits a concentrated light source that puts out a straight line beam of light in a single color. The laser detector is sensitive to light, and is connected to sensing electronics. When the laser beam is interrupted, and cannot reach the detector, then the sensing electronics may emit a wireless warning signal to the base unit, which can then relay the alert to the user's smart phone or remote control 30 via the internet connection. The laser sensor may be placed across a doorway, so that if the door is opened, the laser beam is broken, and an alert is generated. The laser sensor may also be placed in any other desired location, such as a hallway, so that anyone walking or crawling along the hallway would necessarily have to break the beam, thereby triggering the alarm.

Another component that may be used is a magnetic door monitor 26. The magnetic door monitor typically contains two components, one of which is fixed to the door frame, and the other which is fixed to the door. The components are arranged so that when the door is closed, the components are physically positioned adjacent to one another, and a magnetic connection is formed. When the door is opened, the magnetic connection is broken, and the magnetic door monitor 26 senses the broken connection, thereby generating an alarm, which is wirelessly transmitted to the base unit 22 and relayed to the user via the remote control 30. Of course, any type of door sensor or monitor 26 may be used, so long as it can be battery operated, sense the opening and closing of a door, and wirelessly transmit that information to the base unit 22. There are many types of door monitors 26 that may be suitable. Similar types of window monitors or sensors 28 may be used on windows, as well, to trigger an alarm if the window is opened.

It is contemplated that the system may be monitored by a security company or any other security entity that is designated by the user. In such a case, any alert that is generated by the system may be simultaneously sent to the user, multiple users, the security company, or any combination thereof. Alternatively, the system may be set up so that a user or multiple users are alerted by the system first, and then the user may elect to alert the security company after doing a preliminary investigation, in order to reduce or eliminate potential false alarms.

If the system is monitored by a security company, another component may be used. A wireless panic button 34 may be placed in any desired location, so that a user may alert the security company in the event of an intruder (or any other emergency) while the user is inside the house. The panic button 34 simply includes a transmitter that is capable of transmitting an alert signal to the base unit 22, which then relays the signal via the internet (through the wireless internet network, or the cellular data network) to the monitoring company, or any other desired recipient. In a preferred embodiment, the panic button 34 is battery operated, and may be attached to any wall or surface using adhesive, screws, or any other suitable attachment means. The system may be programmed to trigger other events when the panic button 34 is pressed, such as switching on desired lights that are plugged into the sensor units 10 and/or base unit 22, and may activate any or all of the sensor unit 10 and/or base unit 22 cameras 16 to begin recording footage, which can then be saved and sent to the user or the security company.

It is also contemplated that any data collected from the system, including camera footage, alerts generated, or other data, may be transmitted by the base unit 22 to a remote server 36 (the "cloud") via the wireless network or cellular data network. All recorded events may include a time and date stamp, as well as the location (or specific sensor unit 10) that triggered the recorded event. In this way, a user or law enforcement personnel may be able to access the recorded data for investigation purposes. It is further contemplated that a user may access this recorded information by using the software app on a smart phone or tablet.

Home Systems Monitoring

Another aspect of the present system is the ability to monitor various systems in the home, in order to make sure that all systems are working properly, whether the user is at home or away. Users could be advised if the power has gone out, if there is a water leak, or if the wireless network for the internet has become temporarily disabled. In a preferred embodiment, each component of the system (base unit 22, sensor units 10, etc.) are either solely battery powered, or include a battery backup in case the power is shut off. Preferably, battery backup systems include rechargeable batteries, so that in the event of a power outage, the batteries are used to power the system, but may then be recharged when power is restored. Further, it is contemplated that each component include a power monitor, which can generate an alert to the user via the remote control 30 when the battery reaches a certain point (10% power remaining, for instance). This information, in a preferred embodiment, may also be monitored at will by a user by utilizing the software app.

Further, in a preferred embodiment, the base unit 22 may include means for connecting to the internet through a standard wireless (wifi) network from a standard wireless router, and may also include the capability to access the internet using a cellular data network, similar to smart phones and tablets commonly found today. In this way, if the wireless router or wifi network experiences problems or an outage, the system may then use the cellular data network to continue sending alerts and receiving user instructions. Indeed, if a power outage occurs, or an internet outage occurs, the system may still be capable of sending "Power Outage" or "Internet Connection Failure" alerts to the user via the remote control 30, who can then take appropriate action.

The sensor units 10 may have an array of sensors for monitoring the general operation of the home, particularly if the user is away on vacation, or if the property is a vacation home and is often unoccupied, and the system can be configured to send an alert to the user if any of the sensors detect data that is outside of acceptable parameters. In one embodiment, for instance, a temperature sensor monitors the ambient temperature, and if the temperature drops below 40° Fahrenheit during the winter in a cold climate, then an alert is generated and sent to the user, so that the user may take action to prevent pipes from freezing. Other sensors may include moisture or standing water sensors or water flow sensors, which send out an alert if a pipe is broken or leaking, gas detection devices to detect if natural gas or propane is leaking, smoke detectors, carbon monoxide detectors, or any other type of monitors that are capable of sending a wireless signal to the base unit 22. Similarly to some of the security components listed above, these home system monitoring components may either be battery operated, or may have a battery backup, but preferably will still operate, at least temporarily, in the event of a power outage. Most, if not all, of the sensors, monitors or detectors are commonly available on the market today, and it is noted that one skilled in the art would be capable of providing wireless communication to these monitors in order to incorporate the monitors into the present monitoring system. Additionally, in a preferred embodiment, the system is programmable by a user, so that the monitored parameters may be set by the user. Moreover, a user may select components a la carte to be used in their personal system, may program various responses to triggered alerts, and may program the parameters that determine when and under what circumstances an alert is sent.

Personnel Monitoring

In one preferred embodiment, the system may be used to monitor the health and activity of a person, particularly if the person is elderly, infirm, or at risk due to a medical condition. Although it is possible to conduct some limited monitoring using the base unit 22 and sensor units 10 described above, specifically by using the motion sensors 18 to detect a person's movement about the house or apartment, in a preferred embodiment, the system includes a wearable device 38 that tracks the wearer's activities and communicates data to the base unit 22.

It is becoming increasingly common for people to use wearable devices 38 to monitor certain vital signs and track physical activity on a daily basis. Devices such as Apple Watches, Fit-Bits, Jawbones and Garmin Vivofits are examples of such wearable exercise trackers, and many of these wearable devices 38 are configured to wirelessly communicate with other devices, such as smart phones, tablets or computers. Typically, these wearable devices 38 measure vital signs of the wearer, including heart rate, blood pressure, and the like, and they further track and record physical activity, such as the number of slops taken or flights of stairs climbed in a day (or specified lime period).

In the present system, a wearable device 38 is configured to communicate with the base unit 22, and the results or data may be sent to another person or entity, such as a family member, medical professional, monitoring service, or caregiver via smart phone, tablet, computer, or other internet connected device. Additionally, the system may be programmed with certain parameters, so that if any of the data tracked and communicated by the wearable device 38 falls outside the acceptable parameters, then the system generates an alert that is sent to a desired recipient (again, a family member, doctor, or caregiver, for instance). As an example, if the wearer's heart rate is higher or lower than acceptable parameters as detected by the wearable device 38, then the system sends an alert to the designated recipient, who can then take appropriate action to check on the health and well-being of the wearer. Other parameters may be set, as well, including number of steps taken or simply motion in general, in order to make sure that the wearer is at least moving about. These parameters may be set by using the remote control device 30 and/or a touchscreen 32.

In one embodiment, the system may be configured to use a person's phone or tablet, rather than (or along with) the wearable device 38, to monitor physical activity of a person. Because most smart phones include accelerometers and other sensors for detecting motion and physical activity, this information may be communicated to the base unit 22, in order to make sure that the monitored person is in an active state. In this embodiment the software app may simply access the physical activity data that is already being collected by the phone, and may relay that information to the base unit 22. As long as the physical activity data being transmitted to the base 22 unit is within acceptable parameters, then no alert is sent. However, if there is no physical activity detected for a predetermined or programmed amount of time, either from the smart phone, tablet or a wearable device 38, then an alert is generated by the system and sent to a designated recipient.

If an alert is received by a designated recipient, then that recipient may use the remote control 30 to access the cameras 16 throughout the home (on the base unit 22 and/or sensor units 10), for instance, in an attempt to visually locate the wearer, in order to get some preliminary information and assess the situation. The recipient may also attempt to call the wearer on the telephone, or may take whatever action they deem necessary to check on or assist the wearer.

Smart Home System

Another aspect of the present invention is the ability to automate and control various appliances and systems through the use of the wireless remote control 30, which may be a dedicated unit, similar to the remote control of a television or entertainment system, or more preferably, is a smart phone, tablet, computer or the like with a software app developed specifically for this purpose. In one preferred embodiment, the remote control 30 not only receives alerts and messages based on the security and monitoring functions of the system, but can also be used to access the cameras 16 in the base unit 22 and sensor units 10, so that the user can see on the screen of the remote control 30 whatever the selected camera 16 can see in real time, on demand. In this way, the user can activate the app on her smart phone (remote control 30), select any of the cameras 16 that are incorporated into the system, and activate that camera 16 so that images from that camera 16 are displayed on the remote control 30 screen.

Secondly, the user may remotely select, by using the remote control 30, any of the smart outlets 12 housed in the base unit 22 or the sensor units 12, and switch those smart outlets on or off. Thus, anything that is plugged into a specific smart outlet 12, such as a light, television, coffee maker, or any other electrical device, may be switched on or off. The system may also include a dimming capability for lights, so that a user may be able to not only switch a particular light on or off, but may also dim the light to any desired level remotely.

The remote control 30 of the base unit 22 and sensor unit 10 smart outlets 12 may be particularly advantageous in vacation homes or rental properties, where the user could plug a refrigerator, for instance, into one of the sensor units 10, and switch the refrigerator off while the property remains unoccupied, but may switch it on at any time before or during a time when the rental property is to be occupied.

It is also contemplated that the remote control 30 may be used to set timers on each individual smart outlet 12 of the base unit 22 and sensor units 10, so that the user can program specific lights to switch on at some desired time, and then switch off at some later time, in order to make an unoccupied property appear to be occupied. The times may be programmed by the user to change on different days, or may be simply controlled manually via the remote control 30. For instance, if a user wishes to access a camera 16 in a specific room, the user may also switch on one or more lights in that room via control of the smart outlets 12 in order to better view the room with the camera 16. It is contemplated that the remote control unit 30 or app may indicate which specific smart outlets 12 are currently in the "on" position, and which ones are currently in the "off" position.

Another aspect of the smart house programming is a "Good Night" feature, which can he programmed as a macro function. The Good Night feature allows a user to program a specific set of smart outlets 12 to switch off with the press of a single button on the app, and may simultaneously activate the security features in "Home" mode. In this way, once the system is properly programmed, when a user climbs into bed at night, she may select the Good Night button on the remote control 30, and all of the programmed smart outlets switch off, while the security features are activated. These programmed smart outlets 12 may control lights throughout the house, televisions, stereos, or any other appliance that would normally be shut down during overnight hours.

The smart house function of the system may be divided a Landlord function and a Tenant function, where a Landlord has full access to the entire system (including cameras 16) so long as a tenant is not occupying a building, but has only limited access when a tenant is occupying a building (no camera 16 access, for example). The tenant may use the Tenant function of the app on the remote control 30, which allows the tenant to use the security and smart house features during the tenancy, but the Tenant function expires at the end of the tenancy, so that the tenant no longer has any access to or control over the system.

The smart house functionality of the system is programmable in other ways, as well. For instance, a user may plug lights into a sensor unit 10, and program the sensor unit 10 smart outlets 12 to switch on the lights whenever motion is detected in the room by the motion sensor 18. In this way, when any person enters a room, the lights automatically switch on without the user having to find a light switch. The lights can be programmed via remote control 30 to stay on for a specified amount of time, or may be programmed to stay on only until some time period after no further motion is detected.

In one embodiment, the software app on the remote control 30 allows each sensor unit 10 to be specifically named or identified by the user (Den, Master Bedroom, Guest Bedroom, or any desired name), and each specific smart outlet 12 to be named or identified, as well (Den—outlet 1, or Den—outlet 2, etc.), or the smart outlets 12 may be identified by the appliance that is plugged into that smart outlet 12 (Den—floor lamp, or Kitchen—coffee maker). In this way, a user can easily identify the appliance or outlet that she wishes to program or control on the software app of the remote control 30.

System Programming by User

In one embodiment, various aspects of the system can be programmed by the user, preferably using the software app on the user's remote control 30, or on the keypad or touchscreen 32.

Timers

First, a user may select any of the smart outlets 12 that are incorporated into the system, and set a timer for that smart outlet 12 to switch on or off. Different times may be set for different days. Further, a user may select a series of individual smart outlets 12 to be switched on or off by the same timer. The timer may be changed or modified at any time by the user, as with all other programmable features.

Security Sensors

The system may also be programmed, in a preferred embodiment, to react to security sensors as desired by the user. For example, in response to motion being detected, a user may program a smart outlet 12 or a series of smart outlets 12 to switch to the on position, in order to cut on lights that are plugged into those specific smart outlets 12. The user may also program the type of alert that she wishes to receive, whether it is through the software app, via text message, email message, audio alarm from the base unit 22 and/or sensor units 10, some combination thereof, or in any desired way. The user can program the sensor unit 10, upon alert from a motion sensor 18, to activate the camera 16 to take a picture, a series of pictures, video, or simply to activate the camera 16 to show real-time footage to remote control device 30. The user can choose to have the pictures and/or video recorded and saved on a remote server 36, or on the remote control device 30, or both.

Macro Functions

Another feature of the present system is the ability for a user to program a series of actions based on a single command (or the press of a single button or icon on the remote control device 30). For example, a user may program the system to go into "Goodnight" mode by selecting a plurality of individual smart outlets 12, and causing those chosen smart outlets 12 to switch off, along with activating the security features in the "Home" mode by pressing a "Goodnight" mode icon. Similarly, a "Good Morning" mode can be programmed to switch those same smart outlets 12 back on and deactivate the security features. In this way, a user can climb into bed at night, click on the Goodnight mode icon on the remote control, and various lights, televisions, or any other selected appliances may be shut down for the evening, while the security features become activated. Then, in the morning, a user may click on the Good Morning icon, and those appliances switch back to the "on" position, and the security features become deactivated.

Similarly, a user may program the system so that a single icon or button on the remote control 30 switches on all (or a selected number) of the smart outlets 12 in a particular room. For instance, a user may select a number of smart outlets 12 in the user's Den, and program an icon that the user may name "Den" to switch all of the smart outlets 12 (or selected smart outlets 12) on or off at one time. In this way, if a user wishes to enter the Den at night, she can simply click the "Den" icon, and have all of the lights in the Den switch to the "on" position.

Although the present invention has been described in considerable detail with reference to certain preferred versions thereof, other versions are possible. Therefore, the spirit and scope of the appended claims should not be limited to the description of the preferred versions contained herein. All features disclosed in this specification may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A portable wireless remote monitoring system, said system comprising:
    a base unit;
    at least one sensor unit, wherein said sensor unit and said base unit include means for two-way communications, so that said base unit and said sensor unit may wirelessly communicate with one another;
    said sensor unit including a remotely controllable motion sensor, a remotely controllable camera, and at least one remotely controllable electrical outlet, ID each operationally connected to one another;
    a remote control device including a video touch screen and means for two way digital communication with said base unit;
    wherein said motion sensor, upon detecting motion, is configured to activate said camera to record a digital image, and wherein said sensor unit wirelessly transmits said digital image to said base unit, which then wirelessly transmits said digital image to said remote control in a form of a security alert;
    wherein said remote control is configured to wirelessly operate said remotely controllable electrical outlet between an on and off position, and wherein said remote control is further configured to activate and deactivate said motion sensor and said camera; and
    wherein said remote control is configured to receive and simultaneously display real time streaming video imagery generated by said camera on command by a user.

2. The portable wireless remote monitoring system set forth in claim 1, wherein said base unit includes means for providing a data connection to a global computer network, and wherein communication between said base unit and said remote control occurs via said global computer network.

3. The portable wireless remote monitoring system set forth in claim 2, further including a remote computer server connected to said global computer network;
    wherein said base unit and said remote control unit are operationally connected to said remote computer server; and
    wherein said base unit is configured to wirelessly transmit said video image and said security alert to said remote computer server for recording, storage, and later access and retrieval.

4. The portable wireless remote monitoring system set forth in claim 1, wherein said sensor unit further includes a microphone for detecting and recording sound;
    wherein said sensor unit is configured to wirelessly transmit a sound file to said base unit and then to said remote control as part of said security alert when motion is detected by said motion detector; and
    wherein said microphone may be accessed at will simultaneously with said camera via said remote control, so that a user may view video footage and hear corresponding sound detected by said microphone in real time on command by said user.

5. The portable wireless remote monitoring system set forth in claim 1, further including at least one door monitor for monitoring whether a door is in an open or closed position;
    said door monitor having a wireless transmitter that communicates with said base unit, so that when a door is in an open position, said transmitter wirelessly transmits an alert to said base unit, and said base unit then wirelessly transmits an alert to said remote control.

6. The portable wireless remote monitoring system set forth in claim 1, wherein said system further includes a monitoring device selected from the group consisting of a temperature sensor, a humidity sensor, a smoke detector, a toxic gas detector, a standing water monitor, a water flow monitor, and any combination thereof;
    said monitoring device including a wireless transmitter that communicates with said base unit, so that when said monitor detects a programmed condition, said transmitter wirelessly transmits an alert that identifies said programmed condition to said base unit, and said base unit then wirelessly transmits said alert to said remote control.

7. The portable wireless remote monitoring system set forth in claim 6, wherein said monitoring device is battery operated and includes a battery power monitor; and
    wherein said monitoring device is configured to wirelessly transmit a low power alert to said base unit when said battery reaches a predetermined low power level; and
    wherein said base unit wirelessly transmits said low power alert to said remote control.

8. The portable wireless remote monitoring system set forth in claim 1, wherein said system further includes a wearable monitoring device;

said wearable monitoring device including at least one sensor selected from the group consisting of a temperature sensor, a blood pressure sensor, an accelerometer, a heart rate sensor, and any combination thereof;

said wearable monitoring device being powered by a rechargeable battery and including a wireless transmitter to communicate with said base unit so that when said wearable monitoring device detects a programmed condition, said transmitter wirelessly transmits an alert that identifies said programmed condition to said base unit, and said base unit then wirelessly transmits said alert to said remote control.

9. The portable wireless remote monitoring system set forth in claim 1, wherein said sensor unit includes a plurality of remotely controllable electrical outlets;

wherein said remote control is configured to allow a user to program said system to operate said remotely controllable electrical outlets individually, together, or in any combination;

wherein said remote control is configured to allow a user to program said system to switch on or off said remotely controllable electrical outlets by using a timer to turn on said outlets at a specific time and to turn off said outlets at a specific time, either individually, together, or in any combination; and wherein said remote control is configured to allow a user to program said system to switch on or off said remotely controllable outlets in response to detection of motion by said motion detector, either individually, together, or in any combination.

10. The portable wireless remote monitoring system set forth in claim 2, wherein said means for providing a data connection to a global computer network includes at least two separate connections;

wherein one of said connections o said global computer network is via a wifi network connection, and wherein another of said connections to said global computer network is through a cellular data internet connection, independently of said wifi network connection, so that if either connection fails or becomes disrupted, said system can use the other connection to said global computer network to send an alarm to said user, alerting said user that one of said connections to said global computer network is not functional.

11. The portable wireless remote monitoring system set forth in claim 1, wherein said system further includes a remote touchscreen unit that is configured to operate said system;

wherein said touchscreen unit includes means for wirelessly communicating with said base unit, so that a user may input commands and instructions into said touchscreen unit, and said touchscreen unit relays said input commands and instructions to said base unit to be carried out; and wherein said touchscreen unit is configured to receive alerts and other data from said base unit, and to display said alerts and other data thereon.

12. The portable wireless remote monitoring system set forth in claim 11, wherein said touchscreen unit further includes a camera, a microphone, and a speaker, so that a user may use said touchscreen unit to communicate in real time with another user who is using a remote control unit, and wherein said real time communications include both streaming audio and video signals.

13. The portable wireless remote monitoring system set forth in claim 1, further including a remote computer server that is in wireless communication with said base unit;

wherein said remote computer server receives and records data sent from said base unit in response to any alerts generated by said base units; and wherein said remote computer server receives and records data generated by said base unit in response to instructions sent to said base unit by said remote control.

14. The portable wireless remote monitoring system set forth in claim 1, wherein said sensor unit includes an audio speaker that is activated upon detection of motion by said motion sensor to emit an audible alarm.

15. The portable wireless remote monitoring system set forth in claim 14, wherein said system further includes a panic button that is in wireless communication with said base unit, so that a user may activate said audio speaker to emit an audible alarm by pressing said panic button.

16. The portable wireless remote monitoring system set forth in claim 1, further including a plurality of sensor units;

wherein said remote control is configured to display an icon representing each said sensor unit said remotely controlled electrical outlet, and wherein said remote control is configured so that a user may program a name or identifier for each sensor unit and each remotely controlled electrical outlet, and wherein said name or identifier is displayed on said remote control.

* * * * *

UNITED STATES PATENT AND TRADEMARK OFFICE
CERTIFICATE OF CORRECTION

PATENT NO. : 9,460,596 B1
APPLICATION NO. : 15/075061
DATED : October 4, 2016
INVENTOR(S) : Moses Page 1 of 1

It is certified that error appears in the above-identified patent and that said Letters Patent is hereby corrected as shown below:

On the Title Page

Item (57), In the abstract, on Line 2 "a base unit" should be changed to "a base unit,".

In the Specification

In Column 2 on Line 33 the term "deactivating" should be changed to "deactuating"--; In Column 3 on Line 1 the term "deactivating" should be changed to "deactuating"--; In Column 3 on Line 2 the term "art" should be changed to "an"--; In Column 3 on Line 10 the term "tor" should be changed to "for"--; In Column 4 on Line 9 the term "tor" should be changed to "for"--; In Column 6 on Line 35 the term "cither" should be changed to "either"--; In Column 6 on Line 65 the term --a window-- should be inserted between the term "having" and "and"--; In Column 8 on Line 8 a --,-- should be inserted after the term "includes"--; In Column 8 on Line 18 the term "intern&" should be changed to "internet"--; In Column 8 on Line 37 the term "lo" should be changed to "to"--; In Column 8 on Line 57 the term "he" should be changed to "be"--; In Column 9 on Line 23 the term "buildin" should be changed to "building"--; In Column 12 on Line 31 the term "slops" should be changed to "steps"--; In Column 12 on Line 32 the term "lime" should be changed to "time"--; In Column 13 on Line 63 the term "he" should be changed to "be"--; In Column 14 on Line 9 the term "into" should be entered between the term "divided" and "a".

In the Claims

In Column 15 on Line 57 (Claim 1, Line 10), the term "ID" should be removed--; In Column 17 on Line 39 (Claim 10, Line 5), the term "o" should be changed to the term "to".

Signed and Sealed this
Twenty-seventh Day of December, 2016

Michelle K. Lee
*Director of the United States Patent and Trademark Office*